(12) United States Patent
Rout et al.

(10) Patent No.: US 8,853,488 B2
(45) Date of Patent: *Oct. 7, 2014

(54) METHODS FOR RAPIDLY TRANSFORMING MONOCOTS

(71) Applicant: Monsanto Technology LLC, St. Louis, MO (US)

(72) Inventors: Jyoti R. Rout, Niantic, CT (US);
Brenda A. Lowe, Mystic, CT (US);
John Purcell, Mystic, CT (US); Anne Spelletich, Pawcatuck, CT (US);
Michael Spencer, Mystic, CT (US);
Melissa Way, Westerly, RI (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,186

(22) Filed: Mar. 8, 2013

(65) Prior Publication Data

US 2013/0239253 A1 Sep. 12, 2013

Related U.S. Application Data

(62) Division of application No. 11/848,648, filed on Aug. 31, 2007, now Pat. No. 8,395,020.

(60) Provisional application No. 60/841,519, filed on Aug. 31, 2006.

(51) Int. Cl.
*C12N 15/82* (2006.01)
*C12N 15/87* (2006.01)
*C12Q 1/68* (2006.01)

(52) U.S. Cl.
CPC ........ *C12N 15/8265* (2013.01); *C12N 15/8201* (2013.01); *C12N 15/8205* (2013.01); *C12N 15/8206* (2013.01); *C12N 15/8207* (2013.01); *C12N 15/8209* (2013.01); *C12Q 1/6876* (2013.01)
USPC ........... 800/278; 800/293; 800/295; 435/410; 435/412; 435/420; 435/430.1; 435/431; 435/469

(58) Field of Classification Search
USPC .......... 800/278, 293, 295; 435/469, 410, 412, 435/420, 430.1, 431
See application file for complete search history.

(56) References Cited

U.S. PATENT DOCUMENTS 5,159,135 A 10/1992 Umbeck
5,563,055 A 10/1996 Townsend et al.
(Continued)

FOREIGN PATENT DOCUMENTS

CN 1206435 A 1/1999
EP 0 672 752 9/1995
(Continued)

OTHER PUBLICATIONS

Sairam et al. "Shoot meristem: an ideal explant for *Zea mays* L. transformation," Genome 46: 323-329 (2003).*
(Continued)

*Primary Examiner* — Susan McCormick Ewoldt
(74) *Attorney, Agent, or Firm* — Dentons US LLP; David Lanzotti, Esq.

(57) ABSTRACT

The present invention provides methods for transforming monocot plants via a simple and rapid protocol, to obtain regenerated plants capable of being planted to soil in as little as 4-8 weeks. Associated cell culture media and growth conditions are also provided, as well as plants and plant parts obtained by the method. Further, a method for screening recalcitrant plant genotypes for transformability by the methods of the present invention is also provided. Further, a system for expanding priority development window for producing transgenic plants by the methods of the present invention is also provided.

35 Claims, 5 Drawing Sheets

(56) References Cited

U.S. PATENT DOCUMENTS

| | | | |
|---|---|---|---|
| 5,569,834 | A | 10/1996 | Hinchee et al. |
| 5,591,616 | A | 1/1997 | Hiei et al. |
| 5,750,870 | A | 5/1998 | Mathews et al. |
| 5,767,368 | A | 6/1998 | Zhong et al. |
| 5,886,244 | A | 3/1999 | Tomes et al. |
| 5,981,840 | A | 11/1999 | Zhao et al. |
| 6,140,555 | A | 10/2000 | Reichert et al. |
| 6,329,571 | B1 | 12/2001 | Hiei |
| 6,420,630 | B1 | 7/2002 | Wilson et al. |
| 6,455,761 | B1 | 9/2002 | Kuvshinov et al. |
| 7,429,691 | B2 | 9/2008 | Zhang et al. |
| 7,682,829 | B2 | 3/2010 | Cai et al. |
| 7,939,325 | B2 | 5/2011 | Adams et al. |
| 8,124,411 | B2 | 2/2012 | Akula et al. |
| 8,513,016 | B2 | 8/2013 | Akula et al. |
| 2003/0082580 | A1 | 5/2003 | Engler et al. |
| 2004/0210959 | A1 | 10/2004 | Armstrong et al. |
| 2004/0244075 | A1* | 12/2004 | Cai et al. ............... 800/278 |
| 2006/0174367 | A1 | 8/2006 | Zhang et al. |
| 2008/0057512 | A1 | 3/2008 | Rout |
| 2008/0118981 | A1 | 5/2008 | Akula et al. |
| 2008/0124727 | A1 | 5/2008 | Rout et al. |
| 2011/0162112 | A1 | 6/2011 | Li et al. |
| 2011/0212525 | A1 | 9/2011 | Adams, Jr. et al. |
| 2012/0180166 | A1 | 7/2012 | Akula et al. |
| 2014/0051078 | A1 | 2/2014 | Rout |
| 2014/0059717 | A1 | 2/2014 | Akula et al. |

FOREIGN PATENT DOCUMENTS

| | | |
|---|---|---|
| EP | 0 897 013 | 2/1999 |
| EP | 0897013 A1 | 2/1999 |
| JP | 10-117776 | 5/1998 |
| JP | 2003-47463 | 2/2003 |
| JP | 2006-508681 | 3/2006 |
| WO | WO 95/06127 | 3/1995 |
| WO | WO 95/06128 | 3/1995 |
| WO | WO 97/41228 | 11/1997 |
| WO | WO 97/48814 A2 | 12/1997 |
| WO | WO 98/51806 | 11/1998 |
| WO | WO 02/37951 | 5/2002 |
| WO | WO 02/102979 | 12/2002 |
| WO | WO 2004/052085 A1 | 6/2004 |
| WO | WO 2006/011959 | 2/2006 |
| WO | WO 2008/028119 | 3/2008 |
| WO | WO 2008/028121 | 3/2008 |

OTHER PUBLICATIONS

Dodds et al. "Experiments in Plant Tissue Culture," 1999, p. 240.*

Snyman et al. "Direct Somatic Embryogenesis for rapid, Cost Effective Production of Transgenic Sugarcane (*Saccharum* spp. Hybrids)," Proc S Afr Sug Technol Assoc (2000) 74, pp. 186-187.*

Sticklen et al. "Invited Review: Shoot Apical Meristem: A Sustainable Explant for Genetic Transformation of Cereal Crops." In Vitro Cell. Dev. Biol. Plant 41:187-200, May-Jun. 2005.*

Akula et al., "High-yielding repetitive somatic embryogenesis and plant recovery in a selected tea clone, 'TRI-2025', by temporary immersion," Plant Cell Reports, 19:1140-1145, 2000.

Cheng et al., "Desiccation of plant tissues post-agrobacterium infection enhances T-DNA delivery and increases stable transformation efficiency in wheat," *In Vitro Cell Dev. Biol. Plant*, 39:595-604, 2003.

English translation of office action dated Sep. 16, 2010, in Chinese Patent Application No. 200780040000.2.

Espinosa et al., "Production of pineapple transgenic plants assisted by temporary immersion bioreactors," *Plant Cell Rep.*, 21:136-140, 2002.

Etienne et al. "Bioreactors in coffee micropropagation," *Brazilian Journal of Plant Physiology*, 18(1):45-54, 2006.

Etienne et al., "Temporary immersion systems in plant micropropagation," *Plant Cell, Tissue and Organ Culture*, 69:215-231, 2002.

Frame et al., "Agrobacterium tumefaciens-mediated transformation of maize embryos using a standard binary vector system," *Plant Physiol.*, 129:13-22, 2002.

Fromm et al., "Inheritance and expression of chimeric genes in the progeny of transgenic maize plants," *Bio/Technology*, 8:833-839, 1990.

Hanhineva et al., "Shoot regeneration from leaf explants of five strawberry (*Fragaria x ananassa*) cultivars in temporary immersion bioreactor system," *In Vitro Cell. Dev. Biol.—Plant*. 41:826-831. 2005.

Ishida et al., "High efficiency transformation of maize (*Zea mays* L.) mediated by *Agrobacterium tumefaciens*," *Nature Biotech*, 14:745-750, 1996.

Kamo, et al., "Embryogenic callus formation from maize protoplasts," *Planta* (1987) 172:245-251.

Kovacs et al. "Monitoring of haploid maize cell suspension culture conditions in bioreactors," *Plant Cell. Tissue and Organ Culture*, 43:123-126, 1995.

Levy et al., "Transient agrobacterium-mediated gene expression in the *Arabidopsis hydroponics* root system for subcellular localization studies," *Plant Mol. Biol. Reporter*, 23:179-184, 2005.

Mitshali et al., "In vitro culture of sugarcane in a liquid temporary immersion system and assessment of potential use in transgenesis," *South African J. of Botany*, 70(2):362-363, 2004.

Mtshali et al., "In vitro culture of sugarcane in a liquid temporary immersion system and assessment of potential use in transgenesis," 30th Annual Congress of the South African Association of Botanists, Durban, Sout Africa, Jan. 19-22, 2004.

Murashige & Skoog, "A Revised Medium for Rapid Growth and Bio Assays with Tobacco Tissue Cultures," Physiol. Plant. 15:473-497. 1962.

Pental et al.,"Somatic Hybridisation using a double mutant of *Nicotiana tabacum*," *Heredity*, 1984, 53(1), 79-83.

Radojevic, "Tissue culture of maize *Zea mays* cudu i. somatic embryogenesis in the callus tissue," Plant Physiol, 119-441, 1985.

Sairam et al., "Shoot meristem: an ideal explant for *Zea mays* L. transformation," *Genome*, 46:323-329, 2003.

Skoog et al., "Chemical regulation of growth and organ formation in plant tissues cultured in vitro," *Symposia of the Society for Experimental Biology*, No. XI, Cambridge University Press, New York, 1957.

Toki et al."Earl infection of scutellum tissue with agrobacterium allows hig-speed transformation of rice," *Plant J.*, 47(6):969-976, 2006.

Wan et al., "Type I callus as a bombardment target for generating fertile transgenic maize (*Zea may* L.)," *Planta* (1995), 196:7-14.

Zhou et al., "In-vitro morphogenesis of corn (*Zea mays* L.)—I. Differentiation of multiple shoot clumps and somatic embryos from shoot tips," Planta, 187:483-489, 1992.

Zhao et al., "High throughput genetic transformation mediated by agrobacterium tumefaciens in maize," *Mol. Breeding*, 8(4):323-333, 2002.

U.S. Appl. No. 13/945,727, filed Jul. 18, 2013, Akula et al.

U.S. Appl. No. 13/973,243, filed Aug. 22, 2013, Rout et al.

Dodds et al. "Formulations of Tissue Culture Media," Table in *Experiments in Plant Tissue Culture*, Third Edition, Cambridge University Press, p. 240, 1999.

Gordon-Kamm et al., "Transformation of Maize Cells and Regeneration of Fertile Transgenic Plants," *The Plant Cell*, ; vol. 2; pp. 603-618; Jul. 1990.

Snyman et al."Direct Somatic Embryogenesis for rapid, Cost Effective Production of Transgenic Sugarcane (*Saccharum* spp. Hybrids)," *Proc S Afr Sug Technol Assoc*, 47:186-187, 2000.

Sticklen et al."Invited Review Shoot Apical Meristem: A sustainable explant for genetic transformation of cereal crops," *In Vitro Cell. Dev. Biol. Plant*, 41:187-200, May-Jun. 2005.

U.S. Appl. No. 14/339,934, filed Jul. 24, 2014, Adams et al.

* cited by examiner

METHODS FOR RAPIDLY TRANSFORMING MONOCOTS

This application is a divisional of U.S. application Ser. No. 11/848,648, filed Aug. 31, 2007, which application claims the priority of U.S. provisional application Ser. No. 60/841,519, filed Aug. 31, 2006, the entire disclosures of all of which are incorporated herein by reference.

BACKGROUND OF THE INVENTION

1. Field of the Invention

The invention generally relates to plant biotechnology. More specifically, it relates to improved methods for transformation of monocots with a gene of interest.

2. Description of the Related Art

Genomics-based approaches in plant biotechnology have enabled identification and isolation of a large number of genes and have necessitated the need for reliable and efficient high-throughput transformation production systems for testing the utility of these genes by transforming them into economically important monocots such as corn. *Agrobacterium*-mediated transformation of monocots such as corn, rice, and wheat is a widely used experimental approach, often with the use of meristematic tissue such as immature embryos as the explants of choice (e.g. Ishida et al., 1996; Zhao et al., 2001; Frame et al., 2002). For rice, transformation of imbibed seeds has also been reported (Toki et al., 2006). To date, the most common methods following the contacting of cells with *Agrobacterium* include: culturing explant tissue such as immature embryos ("co-culture"), possibly including a "delay" or "resting" (non-selective) step, and followed by culture on selection medium containing auxin(s) allowing de-differentiation of cells to form callus. During this callusing phase, transformed resistant callus tissue is selected in the presence of an appropriate selection agent on a selection medium. This is followed by growth of cells under conditions that promote differentiation of the callus and regeneration of the callus into plants on regeneration and rooting media. This process has typically required at least 10-12 weeks to produce plants that can be transferred to soil for further growth. The process also requires several manual transfers of tissue throughout the transformation process and uses several different types of media.

Thus use of standard transformation and regeneration protocols is time consuming and inefficient, and negatively impacts the transgenic product development timeline, given that there is usually a seasonally limited "priority development window" for making decisions regarding which genetic constructs to prioritize for use in larger scale transformation work based on results obtained during initial research. There is therefore a need in the art of monocot transformation to produce transgenic plants quickly to provide more time and flexibility for making research and product development decisions during a priority development window. Such a high throughput system for corn transformation could produce a large number of transgenic plants for testing genes and creating useful plants while lowering material and labor costs.

Further, embryogenic culture responses of different breeding lines differ greatly, limiting the genotypes of crops such as corn that can be transformed. Accordingly, some lines can form embryogenic callus readily, although many, in general, fail to form any embryogenic callus. Such lines are often considered "recalcitrant" lines. This can require use of non-elite lines for transformation, which can require many generations of breeding to produce agronomically-elite transgenic varieties. Thus there is further a need for transformation methods that allow transformation of hitherto "recalcitrant" corn genotypes to allow a wider choice of transformable lines for product development, as well as for screening such genotypes for their potential transformability.

SUMMARY OF THE INVENTION

In one aspect, the invention provides a method for producing a transgenic monocot plant comprising: a) transforming an explant with at least a first selected DNA; b) culturing the explant in a first culture medium comprising an effective ratio of cytokinin and auxin in order to promote development of regenerable structures capable of root and/or shoot formation; and c) culturing the explant in at least a second and/or third culture medium that supports the simultaneous growth of root and shoot tissues, to produce a regenerated transgenic monocot plant; wherein the regenerated transformed monocot plant is produced within about 4-8 weeks of transforming the explant. The method may further comprise, in one embodiment, transferring the regenerated transgenic monocot plant to a plant growth medium. In particular embodiments, the growth medium is a non-sterile matrix, including a non-sterile matrix comprised in a plug.

In certain embodiments, the regenerable structures are formed within about 6-14 days of transforming the explant. In other embodiments, step (b) is completed within about 6-14 days of transforming the explant. In another embodiment, step (b) is carried out for a length of from about 6 to about 12 days. In yet other embodiments, steps (a) and (b) are carried out without proliferating a callus for more than about 10 days to about two weeks following transforming of the explant. In certain embodiments, the first culture medium comprises a bactericidal compound, such as carbenicillin or other compound that inhibits growth of the *Rhizobia*, including *Agrobacterium*, used for transforming the explant. In other embodiments, the second and/or third culture medium comprises sucrose, at a concentration higher than is found in the first culture medium. In particular embodiments, the first culture medium comprises Lynx 1947.

In other embodiments, step (c) comprises culturing the explant in an added plant growth regulator-free liquid culture medium that supports the simultaneous growth of root and shoot tissues, to produce a regenerated transgenic monocot plant. In particular embodiments, the culture medium that supports the simultaneous growth of root and shoot tissues comprises Lynx 2067. In further embodiments, step (c) is begun within about 4-8 weeks of transforming the explant.

In certain embodiments, the ratio of cytokinin to auxin in the first culture medium is from about 0.005 to about 0.03 (w/w). In other embodiments the ratio of cytokinin to auxin in the first culture medium is from about 0.005 to about 0.03 on a molar basis. In particular embodiments the cytokinin may be selected from the group consisting of BAP, zeatin, kinetin, and TDZ; and the auxin may be selected from the group consisting of IAA, 2,4-D, NAA, IBA, and dicamba. In other embodiments, the cytokinin and/or auxin in the first culture medium may comprise a plant growth-regulatory effect equivalent to these amounts and ratios of the above listed cytokinins or auxins.

In yet other embodiments, step (c) further comprises culturing the explant in a second culture medium comprising an increased ratio of a shoot forming growth regulator to auxin relative to the first medium to promote development of root(s) and shoot(s) simultaneously. In particular embodiments the medium of step (c) is Lynx 2068 and/or Lynx 2202.

Certain embodiments of the methods of the present invention may further comprise culturing the explant in a second and/or third culture medium lacking added plant growth regulators. In some embodiments the ratio of shoot forming growth regulator to auxin in the second medium is from about 0.02 to about 0.06 (w/w). In particular embodiments, the second medium is Lynx 2202 or Lynx 2068. In certain embodiments, fresh growth medium is not added subsequent to the start of step (c).

In yet other embodiments, the first culture medium comprises about 0.001 mg/L to about 10 mg/L of cytokinin and about 0.1 mg to about 15 mg/L auxin, for instance about 0.005 mg/L cytokinin to about 0.05 mg/L cytokinin, and about 0.1 mg/L auxin or 0.2 mg/L auxin to about 0.5 mg/L auxin. In still further embodiments, the explant is further cultured on a fourth medium between culturing on the first and the second medium, wherein the fourth medium comprises an effective amount of auxin and cytokinin to promote callus proliferation. In particular embodiments, the fourth medium is Lynx 2063.

In other embodiments, the explant is further cultured on a fifth medium between culturing on the second and the third medium, wherein the fifth medium comprises an amount of cytokinin effective to promote shoot growth. In particular embodiments, the fifth medium is Lynx 2066.

In certain embodiments, transforming the explant comprises bacterially-mediated transformation. In particular embodiments, bacterially mediated transformation is carried out using a bacterium selected from the group consisting of *Agrobacterium* sp., *Rhizobium* sp., *Sinorhizobium* sp., *Mesorhizobium* sp., and *Bradyrhizobium* sp.

In other embodiments, the second and/or third culture medium comprises an amount of auxin that is reduced relative to the amount in the first medium, cytokinin, abscisic acid, or a combination. In a particular embodiment, the second and/or third culture medium comprises less than half as much auxin or auxin-like plant growth regulator activity as the first medium.

In certain embodiments, the first culture medium and culture medium that supports the simultaneous growth of root and shoot tissues are liquid media. In other embodiments, the first culture medium is a semi-solid medium. In particular embodiments, each medium used subsequent to the first culture medium is a liquid medium. In certain embodiments, steps (b) and (c) are carried out in a single container.

In certain embodiments, the monocot plant is a corn, rice, sorghum, wheat, rye, millet, sugarcane, oat, triticale, switchgrass, or turfgrass plant. In a particular embodiment, the monocot is a corn plant.

In another aspect, the invention provides a system for expanding a priority development window for producing transgenic plants, comprising: (a) selecting a candidate DNA segment of interest for producing a transgenic plant based at least in part on data collected in a first field test; (b) preparing a transgenic monocot plant comprising the candidate DNA segment by the method of claim 1; and (c) assaying the transgenic plant for a desired phenotype and/or genotype in at least a second field test conducted in a growing season subsequent to that in which the first field test is conducted. In particular embodiments, one or both of the first field test or second field test are conducted in the midwest United States. In certain embodiments, assaying the transgenic plant comprises measuring agronomic performance. In particular embodiments, the second field test is a hybrid yield test. In yet other embodiments, the second field test is performed two growing seasons after the first field test.

A further aspect of the present invention provides a method for screening cells of a crop plant line for transformability, comprising (a) culturing crop plant explants on a growth medium that supports production of shoot primordia within about 1-2 weeks; (b) culturing the shoot primordia under conditions that support shoot elongation for at least about a further week in the dark to obtain growing shoot tissue and/or plantlets; and (c) culturing the tissue or plantlets of step (b) on a plant growth medium for at least about a further week to obtain shoot buds and/or plants; wherein the transformability of the cells is measured by the ability of shoot primordia to produce shoot buds and/or plants following step (c).

DETAILED DESCRIPTION OF THE INVENTION

The invention provides improved transformation methods that substantially reduce the time required for production of transgenic plants and expands the range of genotypes that can be transformed. In one embodiment, use of liquid media combined with efficient plant-handling procedures and simplified media and culture steps offers advantages such as shorter production time, higher through-put, lower material and labor costs, and ergonomic safety benefits, while maintaining transformation frequency (TF) at a useful level, or even improving TF.

Further, by allowing production of transformed corn plants via such rapid methods, it is now possible to more efficiently use a seasonally-affected priority development window, i.e. for making decisions regarding transformation constructs and events in view of planting seasons at various locations, as well as based on the results of field tests conducted within those locations. These locations include, for instance, the United States Corn Belt, including all or most of Iowa, Indiana, Illinois, and Ohio, and parts of South Dakota, Nebraska, Kansas, Minnesota, Wisconsin, Michigan, Missouri, and Kentucky. This reduces barriers for planning and prioritizing gene-construct and plant transformation-event studies. Thus, shortening a corn transformation protocol from 10-12 weeks to 6-7 weeks or less effectively expands the product development window by 5-6 weeks, allowing for up to twice the transformation capacity in a timeframe such that yield testing of additional transformants initiated during the priority development window is possible in the second growing season subsequent to the occurrence of the transformation event.

In certain aspects, the inventors found that the use of liquid media with a matrix at various steps instead of the commonly used semi-solid media may result in lower TF. However, use of liquid selection and regeneration media with a delay medium containing cytokinin resulted in similar TF as with semi-solid selection and regeneration medium. Therefore, a faster method has been developed by combining previously separate delay and co-culture steps by use of one medium while maintaining/improving the TF. The presence of cytokinin in co-culture and delay medium (the first medium) triggers an early regeneration response while reducing callusing or simultaneous callusing and plant regeneration, thus leading to faster regeneration. The presence of carbenicillin, a bactericidal compound in co-culture medium allows explants to be cultured on the same medium for an extended period i.e. 7-14 days after DNA delivery by *Agrobacterium*-mediated transformation. Further, the traditional separate callus proliferation and selection step(s) can be eliminated, while still achieving an acceptable TF, as explants may be directly transferred to a second and/or third medium that promotes shoot bud primordia growth and development. Thus, importantly, previously "recalcitrant" genotypes that have shown limited embryogenic response and transformability via a callus-based approach may now be directly used as transformation targets, and without further physical manipulation of explant material i.e. sub-culturing with manual transfer to different media, by use of culture regimes as described herein.

The transformation methods described herein provide a significant improvement over the current transformation method known in the art. By using such methods, it was surprisingly found that a transformed plant can be produced within 4-6 weeks after contacting of cells with a transforming agent that is ready for transplanting into a growth matrix such as plug and/or soil and is produced by more efficient procedures and with a broader range of genotypes. In some aspects, the methods also employ liquid medium with a suitable support matrix. Use of the liquid culture reduces the number of transfer steps from six to as few as two or three. Still further, the step of selecting a transformed cell and regeneration can be achieved in a single container until plants are transferred to soil. The methods are thus suitable for a high-throughput automated production system.

Certain monocot genotypes respond poorly to embryogenic culture conditions. That is, embryos, or embryogenic callus leading to efficient regeneration, are not produced under these conditions. Such "recalcitrant" genotypes have transformation frequencies at or near zero when previously described methods are attempted. Thus, the current methods that can be used to transform a wide variety of genotypes, especially recalcitrant lines, provide a wider choice of transformable lines and represent a significant advance in the art.

Further, methods for assessing the transformability of cells of a monocot crop plant line have typically focused on measuring the ability of a given line to produce embryogenic callus under the right conditions. These conventional approaches for screening for embryogenic callus formation utilize immature embryos that are isolated and grown on tissue culture media capable of supporting embryogenic callus formation. Just as important for transformability is the ability of a cell line to sustain such embryogenic callus growth over time, since some cell lines display a brief burst of callus formation, but do not subsequently maintain their embryogenic potential.

Thus, one embodiment of the present invention comprises a novel method to screen crop plant cells for transformability. This method, in one aspect, comprises culturing explants (e.g. maize immature embryos) on a medium capable of producing shoot primordia in a short time (e.g. within 1-2 weeks, for instance within 1 week). The tissues are then transferred to a regeneration/elongation medium for about 2-3 weeks under dark conditions, before being placed on a growth medium for about 2-3 additional weeks. The ability of lines to regenerate shoot buds and/or plants under these conditions indicates their transformation competence by the methods of the present invention, including those in which no callus growth phase is provided, or in which a period of callus growth is substantially reduced from previous cell culture regeneration methods.

A method of the invention in one embodiment also includes exposing a transformable explant to a transforming agent. Suitable explants include transformable plant parts such as callus, cells and embryos. In specific embodiments the explant may be an immature embryo of about 1.0-3.0 mm in length, for instance the embryo size may be between about 1.6-2.6 mm in length, about 8-14 days post pollination (DAP), including an embryo size of about 2.0 mm at about 10-12 days post pollination. The stages of corn embryo development and morphology have been described (e.g. Matthys-Rochon et al., 1998, and references therein).

Suitable transforming agents include plant transforming bacteria carrying a DNA construct to be transferred. Examples of such bacteria include *Agrobacterium* sp., *Rhizobium* sp., *Sinorhizobium* sp., *Mesorhizobium* sp., and *Bradyrhizobium* sp. (e.g. Broothaerts et al., 2005; U.S. patent application Ser. No. 11/749,583). The explant can also be exposed to the DNA construct via direct uptake, microinjection, electroporation, and micro-projectile bombardment, or by any other method known to those skilled in the art.

Typically, a DNA construct includes one or more expression units. These expression units generally comprise in 5' to 3' direction: a promoter, nucleic acid encoding for a useful trait or for gene suppression, a 3' untranslated region. Several other expression elements such as 5' UTRs, organellar transit peptide sequences, and introns (especially for monocots) are usually added to facilitate expression of the trait. Other genetic components that serve to enhance expression or affect the transcription or translation of a gene in a plant are also envisioned for use.

Numerous plant promoters are known to those of skill in the art. Such promoters include but are not limited to the nopaline synthase (NOS) promoter, cauliflower mosaic virus (CaMV) 19S and 35S promoters (e.g. see U.S. Pat. No. 5,352,605), the enhanced CaMV 35S promoter (e35S), a ssRUBISCO promoter, and an actin promoter (e.g. rice actin promoter; see U.S. Pat. No. 5,641,876), among others. The DNA construct may include a second expression unit wherein the nucleic acid encodes a maker protein for selecting, screening, or scoring a transformed cell.

For the practice of the present invention, compositions and methods for preparing and using constructs and host cells are well known to one skilled in the art, see for example, Sambrook, et al. (2000). Methods for making transformation constructs particularly suited to plant transformation include, without limitation, those described in U.S. Pat. Nos. 4,971,908, 4,940,835, 4,769,061 and 4,757,011, all of which are herein incorporated by reference in their entirety.

Normally, the expression units are provided between one or more T-DNA borders on a transformation construct. The transformation constructs permit the integration of the expression unit between the T-DNA borders into the genome of a plant cell. The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, LBA4404, EHA101, or EHA105 carrying a plasmid having a transfer function for the expression unit. Other strains known to those skilled in the art of plant transformation can function in the present invention.

After contacting an explant with a transforming agent, the explant may be cultured on a first medium (e.g. Lynx #1947) that combines the attributes of a co-culture and a delay medium due to the presence of a bactericidal compound such as Carbenicillin. Such a medium comprises a cytokinin and an auxin. By providing an effective amount of plant growth regulators and appropriate ratio of cytokinin to auxin or any other growth regulators that are known to affect callusing and/or shoot bud formation, such a medium allows subsequent regeneration of tissues, including transformed tissues, to begin without requiring a separate callus proliferation phase or a sustained embryogenic response. The effective growth regulator(s) concentrations and/or ratio of cytokinin to auxin could vary from genotype to genotype and the type of plant species used. Subsequent to the first medium, in certain embodiments the explant may be cultured on a growth regulator free medium to promote plant regeneration. In certain embodiments this medium is a liquid medium.

The methods provided by the invention may be carried out using genotypes that are capable of producing a classical embryogenic callus response, as well as for recalcitrant genotypes that fail to show appreciable amount of embryogenic culture response, or sustained culture response, with other previously known culture methods. The culture period on the first medium may be varied depending upon the need for a particular TF. In one embodiment, the culture period on the first medium is from about 6 or 7 to about 10-14 days. Earlier regeneration also reduces the number of clonal (i.e. sister) plants, including non-transformed plants, that tend to arise following callusing and that may make downstream screening less efficient. The cytokinin may be added to the inoculation or co-culture medium. Alternatively, the cytokinin may be produced by a cytokinin synthesis gene such as a gene for isopentenyl transferase (e.g. U.S. Pat. No. 6,294,714) within the explant of a transformed line.

Examples of various cytokinins that are suitable for use either alone or in combination with the present method include 6-Benzyl aminopurine (BAP), kinetin, zeatin, adenosine phosphate, thidiazuron (TDZ) and other cytokinin like compounds. Examples of various auxins that are suitable for use either alone or in combination with the present method include IAA, 2,4-D, NAA, IBA, dicamba, and other auxin like compounds. One of skill in the art of plant cell culture and transformation would be able to determine appropriate levels of shoot forming plant growth regulators and auxins, and appropriate ratios of the two, that are suitable for use with the present invention. For instance, levels of these or other plant growth regulators with a functionally equivalent level of activity as, for instance, BAP and/or 2,4 D in corn or in another crop plant, may be determined by varying the levels of such growth regulators present in growth media while explants are grown in the media, and following the growth of the explants and tissues derived therefrom. Thus, if other plant growth regulators are used, they would nevertheless comprise a plant growth-regulatory effect equivalent to these contemplated amounts and ratios of the above listed cytokinins or auxins.

A dedifferentiated explant comprising at least one shoot primordium can be produced after co-culture/delay on the first medium and may be cultured on a second medium including an increased ratio of a shoot forming growth regulator, such as a cytokinin or ABA, to auxin than the first medium. Alternatively, the second and/or third medium may comprise a reduced amount of auxin than the first medium, and may further comprise an effective amount of sucrose higher than the first medium for reducing proliferation of callus and faster regeneration. For instance, 50 g/L sucrose in the second medium and 60 g/L in the third medium may be utilized. In another alternative, the second medium and/or third medium may comprise an effective amount of a shoot forming growth regulator such as a cytokinin and/or ABA only, with no added auxin or auxin-like activity. Subsequently, the explant may be cultured on a third culture medium comprising little or no plant growth regulators for shoot elongation and root production.

In one embodiment, the method combines the traditional co-culture and delay medium into a first medium thereby reducing the number of media required for transformation and subsequent culture from five to four. In another embodiment, the method eliminates the callus proliferation/selection medium, two regeneration medium, one rooting medium and provides modified regeneration/elongation media that may lack appreciable amounts of added plant growth regulator, thereby reducing the number of media required for transformation from six to three. In yet another embodiment, the method uses only the first medium and the third medium thereby reducing the number of media required for transformation from six to two.

In other embodiments, the first medium is a semi-solid medium and the other media are liquid media. In yet another embodiment, all media used are liquid media. However, it will be apparent to those skilled in the art to use a combination of semi-solid or liquid media and to use only one or more of the modifications provided herein, depending upon their need.

In a specific embodiment, the explant is cultured on the first culture medium, such as Lynx #1947, for about 7-14 days, on the second culture medium, such as Lynx #2202, for about 7 days, and on the third culture medium, such as Lynx #2067, for about 14-28 days. However, the number of days on one or more media can be increased or decreased by visual inspection of the growth of the transgenic plant by those skilled in the art. In another embodiment, the explant is additionally cultured on a fourth medium between the first and the medium for about 14 days and on a fifth culture medium for about 7 days between the and the third culture medium. The fourth medium, such as Lynx #2063, can contain plant growth regulators including auxin, cytokinin, and $AgNO_3$, and is formulated to support callus proliferation. The fifth medium, such as Lynx #2066, can contain cytokinin but generally no auxin, and is formulated to support shoot growth and elongation. In certain embodiments, the added second, third, fourth, and/or fifth media may comprise no effective amount of a plant growth regulator, while promoting the development of regenerated plants. The second or other subsequent media may be liquid, semi-solid, or solid media. In particular embodiments, only two media may be employed, i.e. a co-culture/delay medium such as, for instance, Lynx 1947, and a subsequent medium, for instance derivatives of Lynx 2067 and Lynx 2066 (also described as "third" and "fifth medium" respectively), lacking appreciable amounts of an auxin, in a method to obtain transformed regenerated plants within 4-8 weeks of transformation (For media compositions see e.g. Tables 2, 3).

The number of days on one or more media can be increased or decreased by visual inspection of the explants by those skilled in the art. The invention thus provides a regenerated plant, and parts thereof, that is capable of growth in a soil-based medium or any other non-sterile matrix within 4-6 weeks after the explant from which it is derived was contacted by a transforming agent, such as by transforming an explant with a selected DNA. In a particular embodiment, 4-8 weeks old regenerated plants are transplanted into plugs (Q Plugs by International Horticultural Technologies, Hollister, Calif.) for further growth and development and initial screening, for instance to determine their genotype and/or phenotype with respect to a transgene of interest.

In other embodiments, the second, third, fourth, and/or fifth media also include a selection agent such as the herbicide glyphosate for terminating or at least retarding growth of most of the cells, tissue, or organ into which the DNA construct has not been delivered. Other suitable selection agents that may be used alone or in combination, include, but are not limited to auxin-like herbicides such as dicamba or 2,4-D, MCPA, 2,4-DB, glufosinate, acetolactate synthase inhibitors, protoporphyrinogen oxidase inhibitors, and hydroxyphenyl-pyruvate-dioxygenase inhibitors, neomycin, kanamycin, paramomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Examples of genes providing tolerance to such selection agents are disclosed in Miki and McHugh, (2004).

A variety of plant tissue culture media are known that, when supplemented appropriately, support plant tissue growth and development. These tissue culture media can either be purchased as a commercial preparation or custom prepared and modified by those of skill in the art. Reagents are commercially available and can be purchased from a number of suppliers (see, for example, Sigma Chemical Co., St. Louis, Mo.; and PhytoTechnology Laboratories, Shawnee Mission, Kans.). Examples of such media include, but are not limited to, those described by Murashige and Skoog (1962); Chu et al. (1975); Linsmaier and Skoog (1965); Uchimiya and Murashige (1962); Gamborg et al. (1968); Duncan et al. (1985); McCown and Lloyd (1981); Nitsch and Nitsch (1969); and Schenk and Hildebrandt (1972), or derivations of these media supplemented accordingly. Those of skill in the art are aware that media and media supplements such as nutrients and growth regulators for use in transformation and regeneration are usually optimized for the particular target crop or variety of interest. One may also select various components such as basal salts, vitamins, carbon source from one or the other medium to obtain desired growth and development. Plant growth media used in a prior method (e.g. Cai et al.; U.S. Patent Application Publication 20040244075, and incorporated herein by reference) are shown in Table 1. Preferred media compositions used in the present methods are listed in Tables 2 and 3. Differences between the recipes used in the present invention and the standard recipes used in the conventional methods of monocot transformation are, for instance, that conventional methods use medium that allows callus proliferation and selection, followed by regeneration and growth of the transgenic event. In contrast, the media of the present invention allow just enough callus formation for formation of shoot primordia thereby avoiding chimeric plant formation and allowing efficient selection through simultaneous callus formation and plant regeneration, in a manner to allow high-frequency transformation.

In general, a $1^{st}$ medium may function as a co-culture and delay medium, and comprises plant growth regulators such as an auxin (e.g. 2,4-D), a cytokinin (e.g. BAP), and silver nitrate, as well as acetosyringone to facilitate *Agrobacterium*-mediated transformation. The $1^{st}$ medium may also contain a bactericidal compound such as carbenicillin which allows explants to be cultured on the same medium for an extended period i.e., 7-14 days after contacting the explant with a transforming agent. A $2^{nd}$ medium (e.g. 2202) may also comprise such plant growth regulators, but auxin is reduced. Importantly, this $2^{nd}$ medium may function as a regeneration medium. A $3^{rd}$ medium (e.g. 2067) lacks growth regulators, and functions as a regeneration or shoot elongation medium. A $4^{th}$ medium (e.g. 2063) comprises a similar amount of growth regulators as the $1^{st}$ medium, and may function to support callus proliferation. A low level of a selective agent may also be present, to favor growth of transformed tissue. A $5^{th}$ medium (e.g. 2066) lacks auxin and silver nitrate, and has a low level of cytokinin, and supports regeneration. Alternatively, media added subsequently to the $1^{st}$ medium may comprise no effective amount of a plant growth regulator, while supporting development and growth of a regenerated plant. In a particular embodiment, a different $2^{nd}$ medium with no auxin but some cytokinin (e.g. 2347, 2348, 2415, 2414; see Table 3) may also be employed as the regeneration medium which can support regeneration and elongation in place of the initially described $2^{nd}$ medium (i.e. 2202). Media 2348, 2415, 2414 are essentially the same as 2066 but with silver nitrate, and contain differing amounts of glyphosate. Medium 2347 is essentially the same as 2067, but with silver nitrate and a cytokinin. Modifications of such media may be made by one of skill in the art of plant cell transformation and tissue culture, depending on the species and genotype of the subject explant tissue, while maintaining the described cell culture attributes.

TABLE 1

Media compositions used in a previous method (Cai et al.; U.S. Patent Applic. Publn. 2004/00244075).

| Media Components/L (Suppliers) | 1233 (co-culture) | 1278 (MSW 50 + BAP), (selection) | 1073 (MS/6BA) ($1^{st}$ regeneration) | 1071 (MSOD) ($2^{nd}$ regeneration) | 1084 (rooting) |
|---|---|---|---|---|---|
| MS Basal Salts (Phytotech) | 2.165 g | 4.33 g | 4.33 g | 4.33 g | 2.165 g |

TABLE 1-continued

Media compositions used in a previous method (Cai et al.; U.S. Patent Applic. Publn. 2004/00244075).

| Media Components/L (Suppliers) | 1233 (co-culture) | 1278 (MSW 50 + BAP), (selection) | 1073 (MS/6BA) (1st regeneration) | 1071 (MSOD) (2nd regeneration) | 1084 (rooting) |
|---|---|---|---|---|---|
| MS Vitamins (100X) (Phytotech) | 10 mL | 10 mL | 0 | 0 | 0 |
| MS Fromm Vitamins (1000X)* | 0 | 0 | 1 mL | 1 mL | 0 |
| BAP (Sigma) | 0 | 0.01 mg | 3.5 mg | 0 | 0 |
| Thiamine HCL (Sigma) | 0.5 mg | 0.5 mg | 0 | 0 | 0 |
| 2,4-D (Phytotech) | 3 mg | 0.5 mg | 0 | 0 | 0 |
| NAA (Sigma) | 0 | 0 | 0 | 0 | 0.5 mg |
| IBA (Sigma) | 0 | 0 | 0 | 0 | 0.75 mg |
| Sucrose (Phytotech) | 20 g | 30 g | 30 g | 0 | 20 g |
| Glucose (Phytotech) | 10 g | 0 | 0 | 10 g | 0 |
| Maltose (Phytotech) | 0 | 0 | 0 | 20 g | 0 |
| Proline (Sigma) | 115 mg | 1.38 g | 1.38 g | 0 | 0 |
| Casamino Acids (Difco) | 0 | 0.5 g | 0.05 g | 0.5 | 0 |
| Asparagine monohydrate (Sigma) | 0 | 0 | 0 | 0.15 | 0 |
| Myo-inositol (Sigma) | 0 | 0 | 0 | 0.1 g | 0 |
| Low EEO Agarose (Sigma) | 5.5 g | 0 | 0 | 0 | 0 |
| Phytagel (Sigma) | 0 | 3 g | 3 g | 3 g | 3 g |
| Acetosyringone (Aldrich) | 200 uM | 0 | 0 | 0 | 0 |
| Carbenicillin (Phytotech) | 500 mg | 500 mg | 250 mg | 250 mg | 0 |
| Glyphosate (Gateway Chemical) | 0 | 0.1 mM | 0.1 mM | 0.1 mM | 0.1 mM |
| Silver Nitrate (Sigma) | 3.4 mg | 3.4 mg | 0 | 0 | 0 |
| pH | 5.2 | 5.8 | 5.8 | 5.8 | 5.8 |

*Comprising 1250 mg/L nicotinic acid (Sigma), 250 mg/L pyridoxine HCl (Sigma), 250 mg/L thiamine HCl (Sigma), and 250 mg/L calcium pantothenate (Sigma).

TABLE 2

Media compositions used in various aspects of the present invention.

| Media Components/L (Suppliers) | 1898 | 2232 | 2233 | 1947 (1st) | 2063 (4th) | 2202 (2nd) | 2066 (5th) | 2067 (3rd) | 2068 |
|---|---|---|---|---|---|---|---|---|---|
| MS Basal Salts (Phytotech) | 4.33 g | 4.33 g | 4.33 g | 4.33 g | 4.33 g | 4.33 g | 4.33 g | 4.33 g | 4.33 g |
| MS Vitamins (100X) (Phytotech) | 10 mL | 10 mL | 10 mL | 10 mL | 10 mL | 10 mL | 10 mL | 10 mL | 10 mL |
| Thiamine HCL (Sigma) | 0.5 mg | 0.5 mg | 0.5 mg | 0.5 mg | 0.5 mg | 0.5 mg | 0.5 mg | 0 | 0.5 mg |
| 2,4-D (Phytotech) | 0.5 mg | 0.2 mg | 0.2 mg | 0.5 mg | 0.5 mg | 0.2 mg | 0 | 0 | 0.2 mg |
| Sucrose (Phytotech) | 30 g | 30 g | 30 g | 30 g | 30 g | 50 g | 50 g | 60 g | 50 g |
| Proline (Sigma) | 1.38 g | 1.38 g | 1.38 g | 1.38 g | 1.38 g | 0 | 0 | 0 | 0 |
| Casamino Acids (Difco) | 0.5 g | 0.5 g | 0.5 g | 0.5 g | 0.5 g | 0.5 g | 0.5 g | 0 | 0.5 g |
| pH | 5.8 | 5.8 | 5.8 | 5.8 | 5.8 | 5.8 | 5.8 | 5.8 | 5.8 |
| Low EEO Agarose (Sigma) | 5.5 g | 5.5 g | 5.5 g | 5.5 g | 0 | 0 | 0 | 0 | 0 |
| *Post autoclave additives* | | | | | *Post filter sterilization additives* | | | | |
| Carbenicillin (Phytotech) | 50 mg | 50 mg | 50 mg | 50 mg | 500 mg | 500 mg | 500 mg | 500 mg | 500 mg |
| Acetosyringone (Aldrich) | 200 uM | 200 uM | 200 uM | 200 uM | 0 | 0 | 0 | 0 | 0 |
| BAP (Sigma) | 0 | 0.01 mg | 0 | 0.01 mg | 0.01 mg | 0.01 mg | 0.01 mg | 0 | 0.01 mg |
| Glyphosate (Gateway Chemical) | 0 | 0 | 0 | 0 | 0.2 mM | 0.2 mM | 0.1 mM | 0.02 mM | 0.2 mM |
| Silver Nitrate (Sigma) | 3.4 mg | 3.4 mg | 3.4 mg | 3.4 mg | 3.4 mg | 3.4 mg | 0 | 0 | 0 |

TABLE 3

Examples of other types of $2^{nd}$ medium used in the present invention.

| Media Components/ L (Suppliers) | 2347 | 2348 | 2414 | 2415 |
|---|---|---|---|---|
| MS Basal Salts (Phytotech) | 4.33 g | 4.33 g | 4.33 g | 4.33 g |
| MS Vitamins (100X) (Phytotech) | 10 mL | 10 mL | 10 mL | 10 mL |
| Thiamine HCL (Sigma) | 0 | 0.5 mg | 0.5 mg | 0.5 mg |
| Sucrose (Phytotech) | 60 g | 50 g | 50 g | 50 g |
| Casamino Acids (Difco) | 0 | 0.5 g | 0.5 g | 0.5 g |
| pH | 5.8 | 5.8 | 5.8 | 5.8 |
| Post filter sterilization additives | | | | |
| Carbenicillin (Phytotech) | 500 mg | 500 mg | 500 mg | 500 mg |
| BAP (Sigma) | 0.01 mg | 0.01 mg | 0.01 mg | 0.01 mg |
| Glyphosate (Gateway Chemical) | 0.02 mM | 0.2 mM | 0.05 mM | 0.1 mM |
| Silver Nitrate (Sigma) | 3.4 mg | 3.4 mg | 3.4 mg | 3.4 mg |

To confirm the presence of the DNA construct in the regenerated plant, a variety of assays can be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Once a gene has been introduced into a plant using the present method, that gene can be introduced into any other plant sexually compatible with the first plant by crossing, without the need for directly transforming the second plant. Therefore, as used herein the term "progeny" denotes the offspring of any generation of a parent plant prepared in accordance with the present invention. A "transgenic plant" may thus be of any generation.

The present invention also provides a plant and plant parts produced by the method. Preferably, the plant is a monocot plant. More preferably, the monocot plant is a crop plant selected from the group consisting of: corn, rice, sorghum, wheat, rye, millet, sugarcane, oat, triticale, turfgrass, and switchgrass plants. In a particular embodiment the monocot plant is a corn plant. The plant parts include, without limitation, seed, endosperm, ovule, pollen, leaf, stem, and root. In a particular embodiment, the plant part is a seed. The invention also includes and provides transformed plant cells and tissues produced by the method.

The following examples illustrate the development of this method.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Nucleic Acid Constructs and Transformation Agents

This example describes the making of the DNA constructs and transformation of the DNA constructs into ABI *Agrobacterium* strain (a disarmed C58 strain) used for transformation of corn immature embryos. The plasmid pMON 97367 contains a cp4 gene as the selectable marker and a gus gene as the screenable marker driven by the chimeric rice actin and rice actin promoter, respectively. Strains of *Agrobacterium* were prepared for transformation essentially according to procedures described elsewhere, such as Cai et al. (U.S. Patent Applic. Publn. 2004/00244075).

Example 2

Improving Throuput of Transformation

Figure 1:
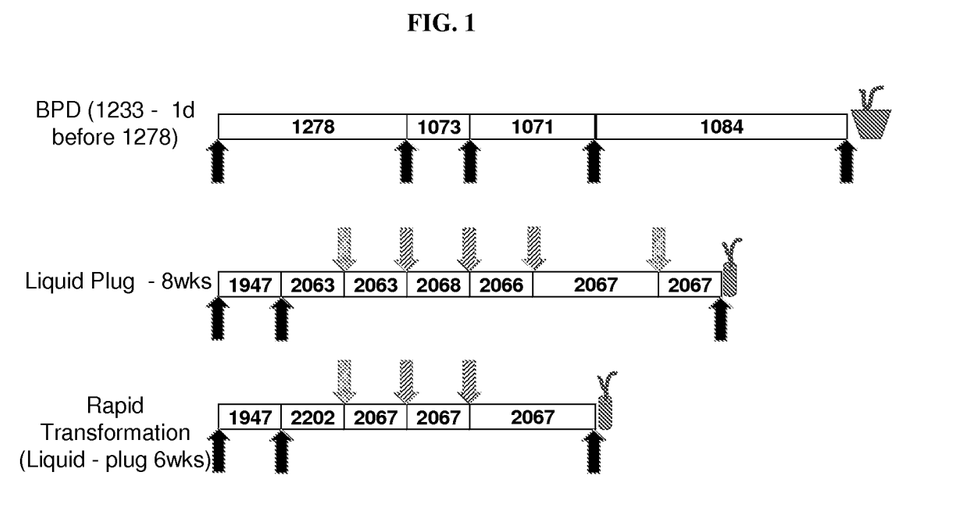
FIG. 1. Line diagram of the control ("BPD") transformation method and two illustrative embodiments of the present invention showing number of culture steps and tissue transfer and media transfer/change steps. One small block represent about one week duration. Dark arrows represent physical transfer of explants to a new container. Arrows with pattern represent aspiration and media change. Arrows with stripes represent addition of media without aspiration.

This example describes the development of a revised method using liquid media during callus proliferation, selection, and during regeneration steps in order to develop a simplified high throughput method needing less tissue handing and which is automatable. FIG. 1 shows an experimental design for this 8 week liquid culture protocol ("Liquid Plug"—FIG. 1, middle diagram). Table 4 shows the results when compared with the method, essentially, of Cai et al (U.S. 2004/0244075, i.e. FIG. 1, top diagram). The revised method is also modified from that found in Example 3, in that explants were transferred to a fourth medium (Lynx 2063) after the first medium for one to two weeks at 30° C. in dark, transferred to a modified $2^{nd}$ medium (e.g. 2068; i.e. 2202 with added $AgNO_3$), and then transferred to a fifth medium (e.g. Lynx 2066) after the second medium for one week at 27° C. in dark.

As noted above, certain corn transformation methods are described in the US Patent Application Publication 2004/0244075 (Cai et al.), and various media composition used are also described therein. Table 4 shows that transgenic plants could be produced within 8 weeks by making modifications to the method of Cai et al., including culturing on the $1^{st}$ culture medium for an extended period, reducing the culture time spent on the $4^{th}$ culture medium, reducing the culture time spent on $5^{th}$ culture medium, and reducing the culture time spent on the rooting medium used in the current method (Table 1). Additionally, the $1^{st}$ $2^{nd}$, $3^{rd}$, $5^{th}$ media were modified (see Table 1 and 2) by adding cytokinin and reducing auxin, by substantially reducing cytokinin and adding a small amount of auxin and increasing sucrose amount, by removing all growth regulators and increasing sucrose, and adding a small amount of cytokinin and auxin and increasing sucrose, respectively. For example, Lynx 1233 used in a conventional method described in Cai et al. does not support prolonged growth and development of explant nor does it support shoot primordia formation like the 1st medium (Lynx 1947) of the current invention. Lynx 1278 of Cai et al. have similar functions as Lynx 2063 of the current invention. The major difference between the two systems is in the area of regeneration. Plant regeneration by the method of Cai et al. uses a high cytokinin pulse step (Lynx 1073), followed by shoot elongation (Lynx 1071) and finally rooting of plantlets accompanied by further growth and development on Lynx 1084. In contrast, regeneration by the current method is achieved by simultaneous development of shoot and root by an auxin step-down approach (Lynx 2068 and Lynx 2066). Final growth and development of the plantlets are achieved on a growth regulator free medium, Lynx 2067.

TABLE 4

Production of transgenic plants within 8 weeks using a liquid media culture method. % TF is the mean of at least 3 independent experiments and is based on % of independent transgenic plant events.

| Treatment | # of explants to selection medium | # Events Produced | TF (%) |
|---|---|---|---|
| Control method | 150 | 55 | 36.7 |
| Liquid media method | 210 | 125 | 59.5 |

Example 3

Transformation Method

This example describes a transformation method, including regeneration steps (FIG. 1, "Rapid Transformation" scheme, bottom diagram), by which is obtained, after about as little as 6 weeks of growth, a regenerated plant in a solid growth medium (e.g. growth plug). In general, immature embryos (IEs) were excised manually or via a fluid jet apparatus such as disclosed in U.S. Pat. No. 7,150,993, or US Patent Application Publn. No. 2005/0246786, and inoculated with the *Agrobacterium* cells containing the DNA construct of interest. The inoculated embryos were cultured on the first medium (Lynx 1947) for about 7 (optionally to about 14) days at 23° C. for 1 day and at 30° C. for the rest of the time in dark, after which explants were transferred to a Petri plate containing a support such as felt and/or filter paper (e.g. Ahlstrom grade 610, 8.22 cm; Ahlstrom Corp., Helsinki, Finland) and 10 ml of a second medium (Lynx 2202), and the plates were incubated at 30° C. under dark conditions for about 1 week. After one week in the presence of the second medium, the old medium was aspirated off and 10 ml of the third medium (Lynx 2067) was added and the plates were incubated at 30° C. in dark for one more week. At approximate one week intervals after the initial transfer to the third medium, old medium was aspirated off and about 15-30 ml of the third medium was added again and plates were incubated at 27-30° C. in 16/8 light-dark. After the 6$^{th}$ week post-transformation, plants were transferred to plugs containing a solid growth medium, under non-sterile conditions for hardening and then to pots for further growth and development within the next 2 weeks. The media compositions used are shown in Table 2.

Example 4

Use of Cytokinin Facilitates Rapid Production of Shoots and Plants

Figure 2:
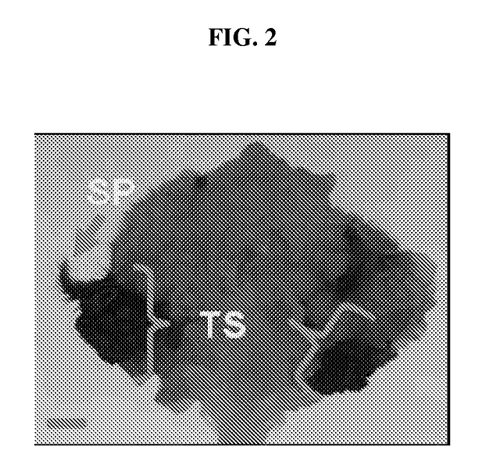
FIG. 2. The presence of cytokinin during the first medium enables efficient and rapid transformation by facilitating production of shoot primordia. Explants were histochemically assayed for gus expression 10 days post transformation and showed large transgenic sectors (TS) and shoot primordium (SP).

This example illustrates the use of cytokinin for initiating early shoot primordia formation for faster production of transgenic plants. Experiments were performed with or without BAP in the first medium (see Table 2 for components) and the results are shown in Table 5. FIG. 2 shows the production of shoot primordia on the first medium. The results also show significant improvement in transformation frequency when the cytokinin was used during this step of the transformation process.

TABLE 5

Use of a cytokinin during the first step of transformation process enhances transformation frequency due to early shoot primordia formation. % TF is average of 4 experiments and is based on % of independent transgenic plant events.

| Treatment (1 week) | # of embryos to selection | Total # Events Produced | % TF Mean ± SD |
|---|---|---|---|
| Lynx 1898; No BAP | 315 | 41 | 13.0 ± 7.4 |
| Lynx 1947; BAP | 365 | 179 | 49.0 ± 2.3 |

Example 5

Simplification of Methods by Decreasing Callus Proliferation and Selection Period This example demonstrates production of transgenic plants within 7 and 6 weeks by decreasing the time spent on Lynx 2063 by 1 week and thus limiting callus proliferation. The outline of the experiment and results are shown in Table 6. The results suggest that a reduced callusing phase can be used without affecting TF. The results also suggested that a further reduction or elimination in callusing phase may be possible which may speed-up the process of transgenic plant production.

TABLE 6

Production of transgenic plants within 7 or 6 weeks by reducing the callusing phase. % TF is the mean of at least 3 independent experiments and is based on % independent transgenic plant events.

| STEPS | Treatment 1 | Treatment 2 | Treatment 3 |
|---|---|---|---|
| Co culture and Delay; 8-10 days | Lynx 1947 | Lynx 1947 | Lynx 1947 |
| 1st transfer; 1 wk | Lynx 2063 | Lynx 2063 | Lynx 2063 |
| 2nd transfer, 1 wk | Lynx 2063 | Lynx 2068 | Lynx 2068 |
| 3rd transfer, 1 wk | Lynx 2068 | Lynx 2066 | Lynx 2067 |
| 4th transfer, 1 wk | Lynx 2066 | Lynx 2067 | Lynx 2067 |
| 5th transfer, 2 wks | Lynx 2067 | Lynx 2067 | plug (6 wks) |
| 6th transfer, 1 wk | Lynx 2067 | plug (7 wks) | N/A |
| 7th transfer | plug (8 wks) | N/A | N/A |
| TF (Mean ± SD) | 16.9 ± 1.0 | 26.0 ± 10.9 | 22.0 ± 5.9 |

Example 6

Development of Six Week Transformation Protocol by Eliminating Callus Proliferation During Selection This example demonstrates the production of transgenic plants within 6 weeks by eliminating the callus proliferation and selection step (Lynx 2063, 4$^{th}$ medium) and one of the regeneration steps, on the fifth medium, completely. The experimental design and the results are shown in Table 7. This experiment included an already shortened method (treatment 1) with one week callus proliferation/selection step on the fourth medium and compared it with a method including direct regeneration on the second medium that contained a lower 2,4-D level than the first medium. Thus in addition to reducing auxin level, an increased ratio of shoot forming growth regulator to auxin is also contemplated. This example demonstrates that the need for callus growth and proliferation step during selection (the fourth and the fifth media e.g. 2063 and 2066 media) can be eliminated and is crucial to obtain transgenic events in a reduced amount of time.

TABLE 7

Production of Transgenic Plants by Eliminating the Callus Proliferation Step. % TF is the mean of at least 3 independent experiments and is based on % independent transgenic plant events.

| STEPS | Treatment 1 | Treatment 2 |
|---|---|---|
| Co-culture and Delay; 8-10 days | Lynx 1947 | Lynx 1947 |
| 1st transfer, 1 wk | Lynx 2063 | Lynx 2202 |
| 2nd transfer, 1 wk | Lynx 2068 | Lynx 2068 |
| 3rd transfer, 1 wk | Lynx 2066 | Lynx 2067 |
| 4th transfer, 1 wk | Lynx 2067 | Lynx 2067 |
| 5th transfer, 2 wks | Lynx 2067 | Lynx 2067 |
| 6th transfer, 1 wk | Lynx 2067 | Plug |
| 7th transfer | Plug | |
| TF (Mean ± SD) | 18.8 ± 9.4 | 40.9 ± 18.7 |

Example 7

Some Callus Proliferation During Co-Culture and Delay is Required for Enhanced TF This example illustrates the role of appropriate cell proliferation of explants during co-culture and delay medium (the first medium) on TF. The callus growth of the explants was controlled by the level of 2,4-D in the co-culture/delay medium. As shown in Table 8 the effect of one week culture on the 1st medium (e.g., 2232, 1947, 2233 or 1898; Table 2) was tested, followed by a six week transformation protocol. It is evident from the results that amount of callusing during co-culture/delay before regeneration determines TF. An auxin level at a lower concentration i.e. 0.2 mg/L in Lynx 2232 had zero TF while explants cultured on 1947 having 0.5 mg/L gave a TF of about 35%. The results suggest that some callus proliferation before growth on $2^{nd}$ medium (including regeneration) is necessary to allow for later shoot bud formation. The amount of callus formation may be optimized by varying the tissue culture parameters including, among others, media components and duration of growth.

TABLE 8

Optimum callus phase during co-culture and delay impacts TF. % TF is the mean of at least 3 independent experiments and is based on % of independent transgenic plant events.

| STEPS | Treatment 1 | Treatment 2 | Treatment 3 | Treatment 4 |
|---|---|---|---|---|
| Co-culture and Delay; 1 wk (7-10 days) | Lynx 2232 | Lynx 1947 | Lynx 2233 | Lynx 1898 |
| 1st transfer; 1 wk | Lynx 2202 | Lynx 2202 | Lynx 2202 | Lynx 2202 |
| 2nd transfer, 1 wk | Lynx 2067 | Lynx 2067 | Lynx 2067 | Lynx 2067 |
| 3rd transfer, 1 wk | Lynx 2067 | Lynx 2067 | Lynx 2067 | Lynx 2067 |
| 4th transfer, 1 wk | Lynx 2067 | Lynx 2067 | Lynx 2067 | Lynx 2067 |
| 5th transfer, 1 wk | Plug | Plug | Plug | Plug |
| TF | 0 | 35.4 | 0.7 | 6.1 |

Example 8

Further Simplifications to Protocol

Figure 3:
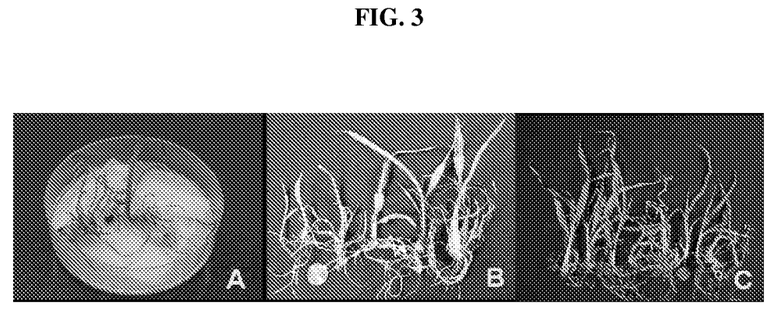
FIG. 3. Four (A), six (B), and seven (C) weeks old transgenic corn plants produced by the method of the present invention.

This example illustrates reducing the duration of growth of explants on regeneration medium (2202) for further simplifying the methods while still allowing obtention of plants within 6 weeks while having no adverse effect on TF. In this study shown in Table 9, the effect of one week each on the second medium (2202; 2068) (treatment 1) was compared with only one week on the second medium 2202 (treatment 2 and 3) followed by elongation on the third medium (2067). The second medium 2202 is identical to 2068 except that 2068 does not have 3.4 mg/L silver nitrate. The third medium (2067) was added at regular intervals (treatment 2) or the spent medium was removed and fresh medium was added (treatment 3). The replacement or dilution of 2202 with 2067 is likely to enhance regeneration. The size range of the plants produced by this method was adequate for transplanting to a plug and had a survival rate of almost 100%. Copy number analysis of nearly 170 events using Taqman® assay on the 3' region of the pin II transcription termination sequence gene present in the expression unit of the DNA construct used for transformation revealed that about 78% of the plants contained 1-2 copy, indicating production of higher percentage of usable plants as compared to only about 60% of plants with 1-2 copies as typically obtained with the current method. Only three plants from the experiment had zero copy indicating very few escapes. Transgenic plants could also be produced for transplanting within as little as 4 weeks as shown in FIG. 3A.

TABLE 9

Production of transgenic plants using a new regeneration and elongation medium. % TF is the mean of at least 2 independent experiments and is based on % of independent transgenic plant events.

| STEPS | Treatment 1 | Treatment 2 | Treatment 3 |
|---|---|---|---|
| Co-culture and Delay; 1 wk (7-10 days) | Lynx 1947 | Lynx 1947 | Lynx 1947 |
| 1st transfer; 1 wk | Lynx 2202 | Lynx 2202 | Lynx 2202 |
| 2nd transfer, 1 wk | Lynx 2068 | Lynx 2067 | Lynx 2067 |
| 3rd transfer, 1 wk | Lynx 2067 | Lynx 2067 | Lynx 2067 |
| 4th transfer, 1 wk | Lynx 2067 | Lynx 2067 | Lynx 2067 |
| 5th transfer, 1 wk | Lynx 2067 | Lynx 2067 | Lynx 2067 |
| 6th transfer | Plug | Plug | Plug |
| TF | 27.1 | 33.8 | 40.6 |

Example 9

Alternative Two and Three Step Protocols

Figure 4:
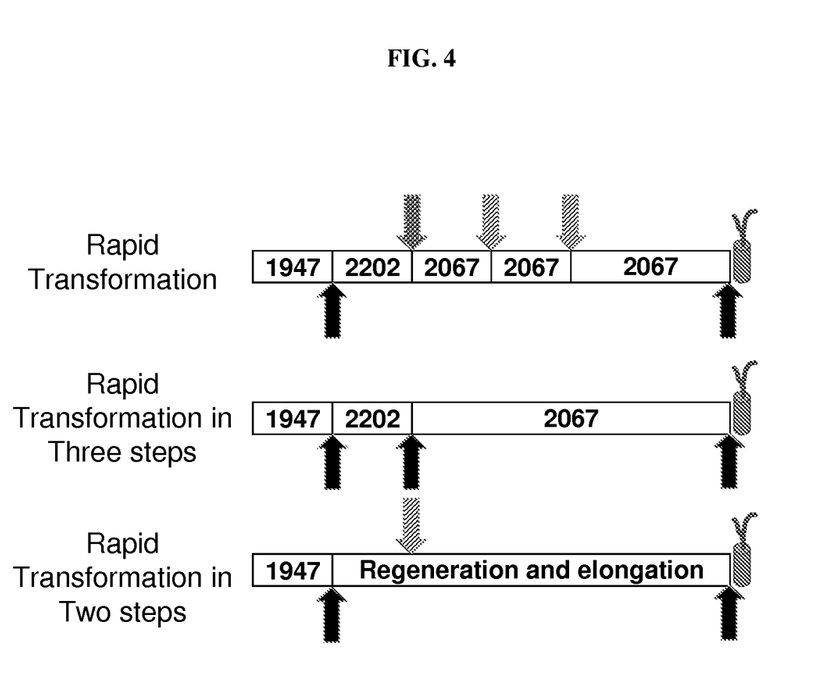
FIG. 4. Line diagram showing further reduction in number of culture steps, tissue transfer steps, and media transfer/change steps. One small block represent about one week duration. Dark arrows represent physical transfer of explants to a new container. Arrows with pattern represent aspiration and media change. Arrows with stripes represent addition of media without aspiration.

This example illustrates production of transgenic plants by further reducing the number of transfer steps and/or aspiration/addition of media steps and/or media as shown in FIG. 4 and in Tables 10 and 11. One important component of the present method is a short callus phase while speeding-up the regeneration at the same time. In this approach, following co-culture/delay ($1^{st}$ medium), tissues were transferred to a regeneration medium ($2^{nd}$ medium; e.g. 2202) for a week to speed-up the regeneration process (Table 10). However, such a step could interfere with easy automation of this method as this $2^{nd}$ medium, comprising auxin which delays elongation, would need to be removed prior to adding the $3^{rd}$ medium (e.g. growth and elongation medium 2067). This issue was overcome by identifying a different second medium without any auxin but some cytokinin (e.g. 2347, 2348, 2415, 2414) as the regeneration medium which can support regeneration, elongation and growth in place of the 2nd medium (i.e. 2202), thereby removing the need to aspirate off the medium. In treatments 2, 3, 4, and 5 after the first transfer, growth regulator free 2067 was added to the containers. The $2^{nd}$ medium used in treatment 5 is a modified version of Lynx 2067 as it contains small amount of BAP and may be used for regeneration and elongation as it does not contain any auxin (e.g. 2347) as shown with the success of treatment 5. Thus, as shown in FIG. 4, bottom, a rapid and simple plant transformation protocol displaying excellent TF, and consisting of only two media steps, is achieved. Furthermore, the ability to simply add medium without aspirating off the old medium makes the system amenable for automation.

TABLE 10

Production of transgenic plants in three culture steps.

| Expt # | Treatment | # plants to selection | Total # Events Produced | % TF |
|---|---|---|---|---|
| 8205-1 | 8 wks-Liquid | 110 | 46 | 41.8 |
| 8205-2 | 6 wks-Liquid | 100 | 38 | 38.0 |
| 8205-3 | 6 weeks-liquid with transformation in three steps | 48 | 20 | 41.7 |

As shown in Table 11, transformation was achieved across all the treatments, indicating that elimination of auxin containing medium (2202) is possible without affecting TF. Additionally, transformation using regeneration and elongation medium comprising no auxin and some cytokinin following the co-culture/delay was possible as shown with 2347, 2348, 2414, and 2415 contain glyphosate at the concentration shown in parentheses.

TABLE 11

Experimental design for Testing Production of Transgenic Plants in Two Steps. For media compositions see Tables 2 and 3.

| STEPS | Treatment 1 | Treatment 2 | Treatment 3 | Treatment 4 | Treatment 5 |
|---|---|---|---|---|---|
| Co-culture and Delay; 10 days | | | Lynx 1947 | | |
| 1st transfer; 1 wk, dark 30 C. | 2202 | 2348 (0.2 mM) | 2415 (0.1 mM) | 2414 (0.02 mM) | 2347 (0.1 mM) |
| 2nd transfer; 1 wk, dark 30 C. | | | Lynx 2067 | | |
| 4th transfer; 3 wks, light 27 C. | | | Lynx 2067 | | |
| 5th transfer | | | Plug | | |
| TF ± SD | 48.9 ± 9.5 | 46.5 ± 9.7 | 39.5 ± 12.5 | 40.5 ± 7.5 | 42.5 ± 9.7 |

Example 10

Transformation of Recalcitrant Corn Genotypes

This example illustrates production of transgenic plants using a recipient elite corn variety which was found to possess a poor embryogenic culture response (i.e. is considered "recalcitrant") relative to a control elite genotype commonly used for transformation via method comprising a separate step of callus formation during selection as described by Cai et al. Only one transgenic event was obtained from 6 experiments utilizing about 1172 explants with the control line, whereas two studies utilizing the rapid transformation methods of the present invention resulted in TF's of about 16.9% and 19.5%, indicating that these methods can be successfully applied to recalcitrant lines. In Table 12, % TF is the mean of 4 independent experiments and is based on % of independent transgenic plant events. In some experiments a TF of about 30-40% could be obtained.

TABLE 12

Modified RLC to facilitate production of plants of an elite line in about 6 weeks.

| STEPS | Treatment 3 | Treatment 4 |
|---|---|---|
| Co-culture and delay | Lynx 1947 | Lynx 1947 |
| 2nd Transfer (dark 30° C.) | Lynx 2063 (callus proliferation and selection) | Lynx 2202 (regeneration) |
| 3rd Transfer (dark 30° C.) | Lynx 2063 (callus proliferation and selection) | Lynx 2202 (regeneration) |
| 4th Transfer (dark 30° C.) | Lynx 2068 (regeneration) | Lynx 2068 (regeneration) |
| 5th Transfer (light 27° C.) | Lynx 2067 (elongation and growth) | Lynx 2067 (elongation and growth) |
| 6th Transfer (light 27° C.) | Lynx 2067 (elongation and growth) | Lynx 2067 (elongation and growth) |
| To Plug | To Plug | To Plug |
| TF % | 16.9 | 19.5 |

Example 11

Methods for Evaluating Transformability of Corn Lines

This example illustrates rapid identification of genotypes for transformation competence in a few simple steps. In this method, explants are cultured on a medium capable of producing shoot primordia in a short time (medium such as 1947; Table 2). One week post culture, the explants are transferred to a regeneration/elongation medium (e.g. Lynx 2424; Table 13) for 2-3 weeks at 30° C. in dark conditions. Lines producing plantlets can be transferred to a growth medium (e.g. Lynx 2427; Table 13) for a period of 2-3 wks. Lines capable of producing and/or regenerating shoot buds through this screening approach will be amenable to a rapid transformation procedure such as outlined above, without the need for a separate callus formation step during their culture.

TABLE 13

Media Used for Evaluating Transformability of Corn Lines

| Media Components/L (Suppliers) | 2424 | 2427 |
|---|---|---|
| MS Basal Salts (Phytotech) | 4.33 g | 4.33 g |
| MS Vitamins (100X) (Phytotech) | 10 mL | 10 mL |
| Thiamine HCL (Sigma) | 0.5 mg | 0 |
| Sucrose (Phytotech) | 50 g | 60 g |
| Proline (Sigma) | 1.38 | 0 |
| Casamino Acids (Difco) | 0.5 g | 0 |

TABLE 13-continued

Media Used for Evaluating Transformability of Corn Lines

| Media Components/L (Suppliers) | 2424 | 2427 |
|---|---|---|
| Adjust pH to | 5.8 | 5.8 |
| Phytagar (Gibco) | 6 | 5.5 g |
| Post autoclave additives | | |
| BAP (Sigma) | 0.01 mg/l | 0 |

Example 12

Reduced Product Development Cycle Time via Rapid Transformation

The invention also provides an expanded priority development window for transgenic plant product development. Such product development is a lengthy process—it can take a minimum of 7-8 years to proceed from an idea and a gene to a commercial product in the form of hybrid corn seed sold to growers. The field of plant biotechnology, and specifically transgenic corn product development, is highly competitive and removing one or more years from a product development cycle can give a company huge returns in market share and revenue.

Figure 5:
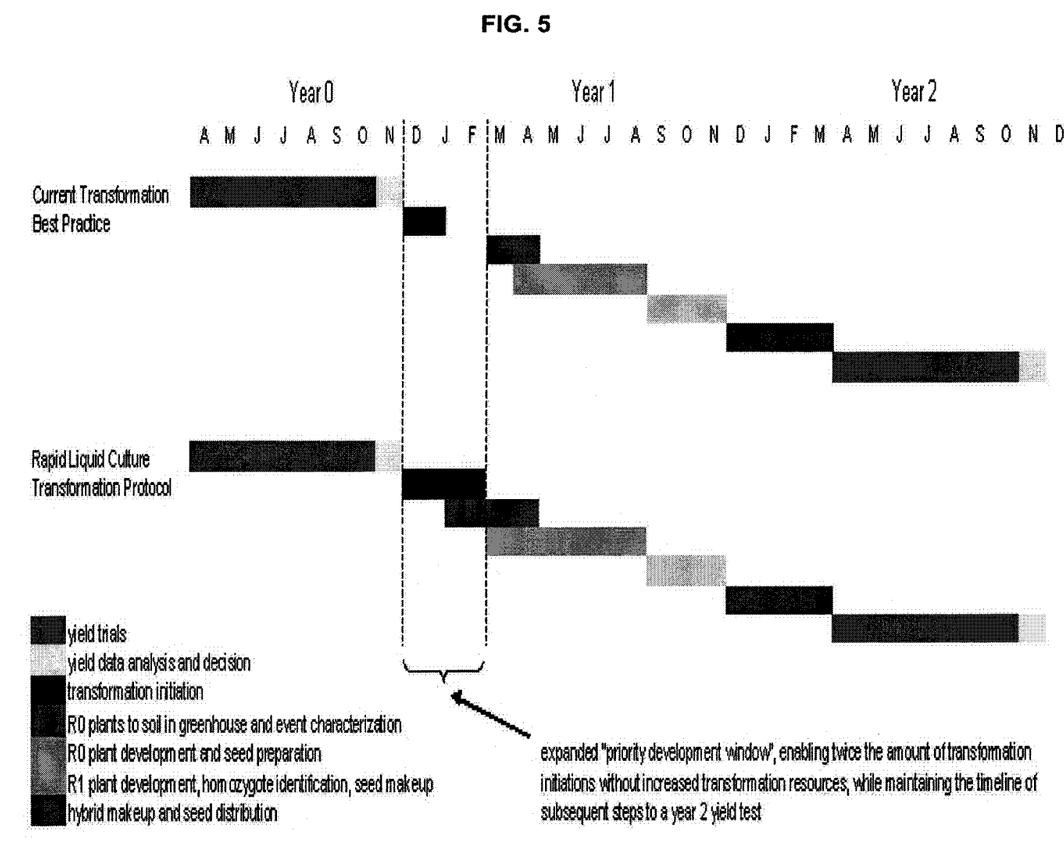
FIG. 5. Impact of Rapid Liquid Culture (RLC) protocol on transformation initiation during the "priority development window".

Using a plant (e.g. corn) transformation protocol that takes about 11-12 weeks to produce transformed plants, the development window typically extends from late November to early January. Subsequent to collection and analysis of Midwest U.S. yield data in any given year, the window of time remaining after data collection to initiate new transformations based on that data, while being able to yield test resulting transformants as hybrids in the second subsequent Midwest growing season is limited to no later than early January, due to the subsequent activities outlined in FIG. 5. These activities include cultivating R0 generation plant and performing event characterization, completion of R0 plant development including pollination and seed preparation, R1 plant development including identification of homozygotes and collection of seed, and finally cultivation of another generation to create hybrids and to distribute seed to field testing locations.

An acceleration of transgenic corn product development is achieved by shortening the time required for corn transformation (time from DNA introduction into cells until plants to soil) such that one full calendar year is removed from the product development cycle of the corn product development pipeline. This is accomplished by shortening the corn transformation protocol from 11-12 weeks or more, to 6-7 weeks or less as shown in blue in FIG. 5. This expands the "priority development window", which is defined as the time from when Midwest U.S. yield data is available in any given growing season until the last possible date at which a transformation can be initiated and transformed lines resulting from these transformations can be yield tested in the U.S. as hybrids, in the second sequential U.S. growing season subsequent to the time of transformation. Yield data generated in the Midwest is critical to U.S. product development regardless of the product. Using a 6-7 week transformation protocol expands the priority development window by 5-6 weeks (FIG. 5), allowing for more time to make business critical decisions or up to twice the transformation capacity with no increase in transformation resources in a timeframe such that yield testing of transformants initiated in the priority development window is possible in the second subsequent growing season (FIG. 5) instead of waiting for a full calendar year before yield testing these transformants.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent they provide exemplary procedural or other details supplementary to those set forth herein, are specifically incorporated herein by reference:

U.S. Pat. Nos. 4,769,061, 4,757,011, 4,971,908, 4,940,835, 4,971,908, 5,352,605, 5,641,876, 6,294,714, and 7,150,993
U.S. Patent Application Publn. 2004/0244075; US Patent Application Publn. 2005/0246786
U.S. patent application Ser. No. 11/749,583
Broothaerts et al., *Nature,* 433:629-633, 2005.
Chu et al., *Scientia Sinica,* 18:659-668, 1975.
Duncan et al., *Planta,* 165:322-332, 1985.
Frame et al., *Plant Physiol.,* 129:13-22, 2002.
Frame et al., *Plant Cell Rep.,* 25:1024-1034, 2006.
Gamborg et al., *Exp. Cell Res.,* 50:151-158; 1968.
Ishida et al., *Nature Biotech.,* 14:745-750, 1996.
Linsmaier and Skoog, *Physiol. Plant.,* 18 100, 1965.
Matthys-Rochon et al., *J. Exp. Bot.,* 49:839-845, 1998.
McCown and Lloyd, *HortScience,* 16:453, 1981.
Mild and McHugh, *J. Biotechnol.,* 107:193-232, 2004.
Murashige and Skoog, *Physiol. Plant,* 15:473-497, 1962.
Nitsch and Nitsch, *Science,* 163:85-87, 1969.
Sambrook et al., In: *Molecular cloning,* Cold Spring Harbor Laboratory Press, Cold Spring Harbor, N.Y., 2000.
Schenk and Hildebrandt, *Can. J. Bot.,* 50: 199-204, 1972.
Toki et al. *Plant J.* 47:969-978, 2006.
Uchimiya and Murashige, *Plant Physiol.* 15:73, 1962.
Zhao et al., *Molec. Breeding,* 8:323-333, 2001.

What is claimed is:

1. A method for producing a transgenic corn plant comprising:
    a) transforming an explant with at least a first selected DNA; then
    b) culturing the explant in a first culture medium comprising an effective ratio of cytokinin and auxin to promote development of regenerable structures capable of root and/or shoot formation; and
    c) culturing the explant in at least a second culture medium comprising a reduced amount of auxin relative to the first medium, and/or a third culture medium that lacks auxin, cytokinin, and silver nitrate, and supports the simultaneous growth of root and shoot tissues, to produce a regenerated transgenic corn plant;

wherein the ratio of cytokinin to auxin in the first culture medium is about 0.02 (w/w) and wherein the regenerated transgenic corn plant is produced within about 4-8 weeks of transforming the explant.

2. The method of claim 1, further comprising transferring the regenerated transgenic corn plant to a plant growth medium.

3. The method of claim 2, wherein the growth medium is a non-sterile matrix.

4. The method of claim 3, wherein the non-sterile matrix is comprised in a plug.

5. The method of claim 1, wherein the regenerable structures are formed within about 6-14 days of transforming the explant.

6. The method of claim 1, wherein step b) is completed within about 6-14 days of transforming the explant.

7. The method of claim 1, wherein steps a) and b) are carried out without proliferating a callus for more than about 10 days to two weeks.

8. The method of claim 1, wherein the first culture medium comprises a bactericidal compound.

9. The method of claim 1, wherein the second and/or third culture medium comprises sucrose at a concentration higher than is found in the first culture medium.

10. The method of claim 1, wherein the first culture medium comprises Lynx 1947 medium of Table 2.

11. The method of claim 1, wherein step (c) comprises culturing the explant in an added plant growth regulator-free liquid culture medium that supports the simultaneous growth of root and shoot tissues, to produce a regenerated transgenic corn plant.

12. The method of claim 11, wherein the culture medium that supports the simultaneous growth of root and shoot tissues comprises Lynx 2067 medium of Table 2.

13. The method of claim 1, wherein step (b) is carried out for a length of from about 6 days to about 12 days.

14. The method of claim 1, wherein step (c) is begun within about 4-8 weeks of transforming the explant.

15. The method of claim 1, wherein the ratio of cytokinin to auxin in the first culture medium is from about 0.005 to about 0.03 (w/w).

16. The method of claim 1, wherein the cytokinin is selected from the group consisting of BAP, zeatin, kinetin, and TDZ; and the auxin is selected from the group consisting of IAA, 2,4-D, NAA, IBA, and dicamba.

17. The method of claim 1, and wherein step (c) comprises culturing the explant in a second culture medium comprising an increased ratio of cytokinin to auxin relative to the first medium to promote development of root(s) and shoot(s) simultaneously.

18. The method of claim 17, wherein the second culture medium of step (c) is Lynx 2202 medium of Table 2 and for Lynx 2068 medium of Table 2.

19. The method of claim 1, further comprising culturing the explant in a third culture medium lacking plant growth regulators.

20. The method of claim 15, wherein the ratio of shoot forming growth regulator to auxin in the second medium is from about 0.02 to about 0.06 (w/w).

21. The method of claim 15, wherein the second medium is Lynx 2202 medium of Table 2 or Lynx 2068 medium of Table 2.

22. The method of claim 15, wherein fresh growth medium is not added subsequent to the start of step (c).

23. The method of claim 15, wherein the first culture medium comprises about 0.001 mg/L to about 10 mg/L of cytokinin and about 0.1 mg to about 10 mg/L auxin.

24. The method of claim 1, wherein the explant is further cultured on a fourth medium between culturing on the first and the second medium, wherein the fourth medium comprises an effective amount of auxin and cytokinin to promote callus proliferation.

25. The method of claim 24, wherein the fourth medium is Lynx 2063 medium of Table 2.

26. The method of claim 24, wherein the explant is further cultured on a fifth medium between culturing on the second and the third medium, wherein the fifth medium comprises an amount of cytokinin effective to promote shoot growth.

27. The method of claim 26, wherein the fifth medium is Lynx 2066 medium of Table 2.

28. The method of claim 1, wherein transforming the explant comprises bacterially-mediated transformation.

29. The method of claim 28, wherein the bacterially mediated transformation is carried out using a bacterium selected from the group consisting of *Agrobacterium* sp., *Rhizobium* sp., *Sinorhizobium* sp., *Mesorhizobium* sp., and *Bradyrhizobium* sp.

30. The method of claim 17, wherein the second culture medium comprises a reduced amount of auxin relative to that found in the first medium, and also comprises cytokinin, abscisic acid, or a combination; wherein the second culture medium comprises cytokinin and/or abscisic acid with no added auxin; and/or wherein the third culture medium comprises cytokinin and/or abscisic acid with no added auxin.

31. The method of claim 30, wherein the second and/or third culture medium comprises less than half as much auxin plant growth regulator activity—as the first medium, or no added auxin.

32. The method of claim 1, wherein the first culture medium and the at least second and/or third culture medium that supports the simultaneous growth of root and shoot tissues are liquid media.

33. The method of claim 1, wherein the first culture medium is a semi-solid medium.

34. The method of claim 1, wherein each medium used subsequent to the first culture medium is a liquid medium.

35. The method of claim 1, wherein steps b) and c) are carried out in a single container.

* * * * *

UNITED STATES PATENT AND TRADEMARK OFFICE
CERTIFICATE OF CORRECTION

| | | |
|---|---|---|
| PATENT NO. | : 8,853,488 B2 | Page 1 of 1 |
| APPLICATION NO. | : 13/791186 | |
| DATED | : October 7, 2014 | |
| INVENTOR(S) | : Jyoti R. Rout et al. | |

It is certified that error appears in the above-identified patent and that said Letters Patent is hereby corrected as shown below:

In the Claims:

Column 23, Line 52, please delete "and for" and insert --and/or--

Signed and Sealed this
Twenty-fourth Day of March, 2015

Michelle K. Lee
*Director of the United States Patent and Trademark Office*